United States Patent [19]
Gordon et al.

[11] Patent Number: 5,622,686
[45] Date of Patent: Apr. 22, 1997

[54] DIAGNOSIS AND TREATMENT OF VIRAL EFFECTS USING MAGNETIC METAL TRANSFERRIN PARTICLES

[76] Inventors: David Gordon, deceased, late of Skokie, Ill.; by Eunice Gordon, legal representative; Robert T. Gordon, both of 4936 West Estes, Skokie, Ill. 60077

[21] Appl. No.: 472,721

[22] Filed: Jun. 7, 1995

Related U.S. Application Data

[62] Division of Ser. No. 195,070, Feb. 14, 1994, which is a continuation of Ser. No. 38,037, Mar. 29, 1993, abandoned, which is a continuation of Ser. No. 792,474, Nov. 15, 1991, abandoned, which is a continuation-in-part of Ser. No. 285,979, Dec. 19, 1988, abandoned.

[51] Int. Cl.⁶ ................................................ A61B 5/055
[52] U.S. Cl. ................. 424/9.32; 424/9.322; 424/646; 424/648; 435/7.8; 436/173; 514/59
[58] Field of Search ................ 435/7.8; 424/9.32, 424/9.322, 646, 648; 436/173; 128/653.4, 654; 514/59

[56] References Cited

U.S. PATENT DOCUMENTS

| | | | |
|---|---|---|---|
| Re. 35,152 | 2/1996 | Rubin et al. ........................ | 128/654 |
| 4,106,488 | 8/1978 | Gordon . | |
| 4,136,683 | 1/1979 | Gordon . | |
| 4,303,636 | 12/1981 | Gordon . | |
| 4,569,836 | 2/1986 | Gordon . | |
| 4,590,922 | 5/1986 | Gordon . | |
| 4,622,952 | 11/1986 | Gordon . | |
| 4,662,359 | 5/1987 | Gordon . | |
| 4,735,796 | 4/1988 | Gordon . | |
| 4,767,611 | 8/1988 | Gordon . | |
| 4,772,548 | 9/1988 | Stavrianpoulos ................... | 435/5 |
| 4,868,106 | 9/1989 | Ito et al. ............................. | 435/7 |
| 4,994,014 | 2/1991 | Gordon . | |
| 5,043,101 | 8/1991 | Gordon . | |
| 5,160,725 | 11/1992 | Pilgrimm ............................ | 424/9 |
| 5,244,785 | 9/1993 | Loor et al. .......................... | 435/5 |
| 5,256,399 | 10/1993 | Sessler et al. ..................... | 424/9 |
| 5,384,109 | 1/1995 | Klaveness et al. ................ | 424/9 |

OTHER PUBLICATIONS

Cremer et al., "Role of Human Immunodeficiency Virus Type 1 and Other Viruses in Malignancies Associated With acquired Immunodeficiency Disease Syndrome" *Journal of the Nat. Cancer Institute*, vol. 82, No. 12, Jun. 20, 1990, pp. 1016–1024.

Sarma et al., "Human T–Cell Lymphotropic Viruses in Human Diseases" *Journal of the Nat. Cancer Institute*, vol. 82, No. 13, Jul. 4, 1990, pp. 1100–1106.

Stryer, *Biochemistry*, 2nd ed. (W.H. Freeman and Company, New York) pp. 740–741 (1981).

*Primary Examiner*—Gary E. Hollinden
*Attorney, Agent, or Firm*—Millen, White, Zelano, & Branigan, P.C.

[57] ABSTRACT

This invention provides methods of treatment and/or diagnosis and/or siting of viruses including the AIDS virus and others as well as the cells which they infect. The method comprises introducing near, into or onto the virus or the cell which the virus infects, or both, minute particles. These particles possess ferromagnetic, paramagnetic or diamagnetic properties. After being localized near, in or on the virus or the viral-infected cell, the particles are inductively heated by application of an alternating electromagnetic field. The inductive heating is continued for a period of time sufficient to bring about a temperature rise to a minimum necessary to kill the virus or cell or to desirably alter the behavior of the virus or infected cell. Prior to, during or after treatment, these particles can be used diagnostically to locate and/or map the virus in the living tissue.

10 Claims, No Drawings

DIAGNOSIS AND TREATMENT OF VIRAL EFFECTS USING MAGNETIC METAL TRANSFERRIN PARTICLES

This is a division of the application Ser. No. 08/195,070, filed Feb. 14, 1994, which is a continuation of Ser. No. 08/038,037, filed Mar. 29, 1993, abandoned which is a continuation of Ser. No. 07/792,474, filed Nov. 15, 1991, abandoned which is a continuation-in-part of Ser. No. 07/285,979, filed Dec. 19, 1988, abandoned.

BACKGROUND OF THE INVENTION

Presently, one of the most serious illnesses facing the world is the viral infection, Acquired Immunodeficiency Syndrome (AIDS). This infection is caused by a virus, designated HIV, or one of its variants. These contain RNA which is coated with a protein shell. The virus affects the T-cells (lymphocytes) of the body as well as other immune-oriented cells (i.e., glial cells in the brain). This effect results in a serious reduction of the body's immunological ability to fight disease and the various bacterial, viral and fungal entities which constantly are in the environment. The fact that a virus becomes a part of cells themselves makes it difficult to affect them adversely without harm to the host. Current methods of treatment involve the use of chemotherapeutic agents. AZT is one choice, but the side-effects are very significant.

The AIDS virus causes problems in an infected individual through the production of alterations in the cell function. These alterations are produced through the interaction of the virus and subcellular components, nuclear protein being one example.

A method of treatment of the virus and vital-infected cells is clearly desirable. To be completely successful, the treatment should kill the invading organism while causing substantially no harm to host tissue. Also, a treatment should produce little or no chance for the organism being treated to become tolerant or resistant to the treatment method.

One method applied to organisms in general, including viruses, is to focus upon a particular aspect of the infectious organism's metabolism which differs from that of the host cells. Rather than interfering with cellular pathways as antibiotics do, this method exploits the organism's routine use of that pathway in such a way that it may be turned against the organism, thus killing it. See U.S. Pat. No. 4,590,922 of R. T. Gordon. However, it is not disclosed that this method is applicable to HIV and related viruses.

This invention relates, inter alia, to a method of treating the AIDS virus, HIV and related organisms (e.g., HTLV and others), or cells infected therewith, comprising providing said organisms and/or cells with minute, inductively heatable, intracellularly localizable particles of a size less than 1 micron and inductively heating said particles by the application of an alternating electromagnetic field (or oscillating or pulsed) for a period of time sufficient to effect a rise in intracellular temperature to a minimum necessary to kill the infectious organisms. Independent investigators have determined that it requires a temperature of approximately 60° C. for a period of 30 minutes to incapacitate or kill the HIV virus. (Spire et al., The Lancet, Jan. 26, 1985, 188; P. Collinson et al., Ann. Clin. Blochem. 1986, 23:102; and Houssein et al., Clinical Chemistry, Vol. 31, No. 12, 1985). This invention readily achieves this selectivity without heating the entire body to this intolerable temperature. In addition to raising HIV temperature to a given level for a time sufficient to kill the virus, the temperature can be raised to a level for a time sufficient to cauterize it. Other temperature levels/times, e.g., sufficient to inactivate the virus can be used also.

The particles best suited for this treatment are pharmacologically acceptable ferromagnetic, paramagnetic, including superparamagnetic, or diamagnetic particles, e.g., suspended e.g., colloidally, in a liquid vehicle. These possess magnetic properties uniquely suited for treatment and diagnostic regimens. Many such particles are disclosed in R. T. Gordon's U.S. Pat. Nos. 4,106,488; 4,136,683; 4,303,636, 4,569,836, 4,731,239, 4,735,796 and 4,590,922, all of which disclosures are fully incorporated by reference herein.

These particles may be selected from ferromagnetic, paramagnetic or diamagnetic inorganic elements and compounds as well as organic compounds such as metal dextran complexes, metal-containing prosthetic groups, transport or storage proteins and the like. The invention may utilize particles exogenously supplied to the infected cells or viral organisms, or particles which are endogenous to the infected cells, e.g., in the form of one of the above-mentioned elements or compounds. The treatment is particularly useful for HIV virus or HIV virus infected cells.

The present invention provides a technique for achieving a precise increment of heat or energy rise within the virus itself or the virus-infected cell. The internal temperature of the invading HIV virus can be raised to the minimum necessary to destroy it. Alternatively, the vital-infected cells can be destroyed or altered so as to resume normal function. In accordance with the present invention, there are a number of approaches which can achieve the end result of destroying the virus affecting the vital-infected cells without causing damage to the host cells.

In its preferred aspect as mentioned above, the invention introduces, near, on or into the virus or the viral-infected cells, minute particles (e.g., less than 1 micron in diameter, e.g., on the order of about 0.1, 1, 10, 100, 1000 or 10,000 Angstroms, or smaller, the precise size not being critical) of a ferromagnetic, paramagnetic or diamagnetic material. By "near" herein is meant sufficiently close to effect the method of this invention.

Minute particles possessing ferromagnetic, paramagnetic or diamagnetic properties have already been shown to be particularly useful in treating cancer, as described by R. T. Gordon, e.g., in U.S. Pat. Nos. 4,106,488 and 4,735,796 mentioned above. As exemplified therein, ferric hydroxide and gallium citrate can be used to form particles of a size of 1 micron or less and may be introduced into the cancer cells in the area to be treated. The cells of the chosen area may then be subjected to a high-frequency alternating electromagnetic field which inductively heats the intracellular particles, resulting in an increase in intracellular temperature. Because the cancer cells accumulate the particles to a greater degree than normal cells, and because they also have a higher resting temperature than normal cells, the increase in temperature kills the cancer cells and leaves the normal cells substantially unharmed. This technique has also been applied by Gordon to infectious diseases including those caused by bacteria, fungi, protozoa and viruses. (U.S. Pat. No. 4,590,922)

The present invention involves the unexpected discovery that, with certain modification where appropriate, the intracellular hyperthermia technique as disclosed by Gordon may be effectively utilized in destroying the HIV virus or altering the infected cells' behavior, e.g., by exploiting the uniqueness and/or specificity of some of the viruses' metabolic pathways and/or magnetically affectable, optionally metabolizable, products, to selectively concentrate magnetic particles within cells infected by the AIDS-causing organisms. The invention also utilizes the technique by selectively focusing the inductive heating process upon magnetic particles found in the HIV viruses or virus-infected cells but substantially not in host cells or therein to a significantly lesser degree. In addition, these particles and methods may be used diagnostically, e.g., to locate viral-containing cells in the appropriate living tissue.

One example of such a selective pathway involves the way in which viruses require iron for the infected cells to survive and proliferate. (This discussion of the invention in relation to iron metabolism is in no way intended to limit this invention which applies generally and not only to iron metabolism.) The necessity of uptake of iron by viral-infected cells is well known (Blumberg et al, Lancet Feb. 11, 1984, pg. 347). Actually, in the AIDS patient, it has been known that serum iron levels fall due to the utilization of Fe by the infectious organisms. Serum ferritin also increases in this condition. In addition, in HIV infections, the T-cell lymphocyte is prominently involved. But the resting T-cell lymphocyte has very few receptors for transferrin, the glycoprotein which binds Fe for transport. However, when the T-cell is infected with HIV, the number of transferrin receptors increases tremendously. This increase in the number of transferrin receptors on the activated T-lymphocytes is very important as will be discussed below.

Another example involves the binding of terbium to the nucleic acid of RNA virus, e.g., as has been shown by Morley et al, Biochem. Biophys. Res. Commun. 101:1123, 1981. The binding of platinum-complexed particles to nucleic acids has also been shown. Moreover, the binding of Pt-Rhodamine complexes to nucleic acid has been demonstrated. Metalloporphyrins also bind to the coating material. All of these pathways can be used in conjunction with this invention, e.g., by including appropriate corresponding chemical entities in the particles of this invention whereby these pathways are entered by the particles resulting in localization of them in, near or on the HIV virus or cells infected therewith. Moreover, when the HIV virus or infected cells contain ferromagnetic and/or paramagnetic elements within them, these endogenous moieties can also be used to produce the effect of this invention.

Particularly useful particles for this invention include, as discussed above, both inorganic elements and compounds as well as metal-containing organic compounds. Inorganic elements and compounds particularly well-suited, owing to their favorable magnetic parameters, comprise elements such as dysprosium, erbium, europium, gallium, holmium, samarium, terbium, thulium, ytterbium or yttrium and compounds thereof, such as dysprosium sulfate, erbium sulfate, europium oxide, europium sulfate, holmium oxide, samarium sulfate, terbium oxide, terbium sulfate, thulium oxide, ytterbium sulfide, yttrium oxide, yttrium sulfate, yttrium ferrioxide ($Y_3Fe_5O_{12}$) and yttrium aluminum oxide ($Y_3Al_5O_{12}$).

Metal-containing organic molecules useful for the application discussed above comprise particles of iron-dextrans such as FeOOH-dextran complexes and other dextran complexes and other dextran metal complexes wherein the metal is selected from the group comprising cobalt, zinc, chromium, nickel, platinum, manganese and rare earth metals such as dysprosium, erbium, europium, gallium, holmium, samarium, terbium, thulium, ytterbium and yttrium, ferric ammonium citrate, enterochelin, hydroxamates, phenolates, ferrichromes, ferritin (e.g., referring to the above, to bind a glycoprotein envelope of a virus), ferric mycobactins, and iron-sulfur proteins such as ferredoxin and rubredoxin.

Particularly appropriate metal-containing organic structures for use with the present invention are the porphyrins such as etioporphyrins, mesoporphyrins, uroporphyrins, coproporphyrins, protoporphyrins, and dicarboxylic acid containing porphyrins and substituted porphyrins such as tetraphenylporphyrin sulfonate (TTPS). Especially advantageous protoporphyrins comprise hematoporphyrins, chlorophylls and cytochromes. In addition to the naturally occurring protoporphyrins which possess iron- or magnesium-containing moieties, mixed metal hybrid porphyrins may also be prepared. For example, by substituting an alternative metal for the iron in hematoporphyrin, the advantages of the porphyrin moiety (e.g., in terms of specificity of localization) is retained while the unique magnetic properties of the new metal enhance the sensitivity of the substituted molecule. Suitable metals for purposes of substitution comprise cobalt, manganese, zinc, chromium, nickel, platinum and rare earth series of metals, dysprosium, erbium, europium, gallium, holmium, samarium, terbium, thulium, ytterbium and yttrium. Suitable porphyrin acceptors comprise any dicarboxylic acid containing porphyrin, such as protoporphyrins (e.g., hematoporphyrins) and the like.

Especially appropriate particles are the $Fe_3O_4$-dextran-transferrin compounds. Included in this group are magnetic particle transferrin compounds where the magnetic particle is ferromagnetic, paramagnetic or diamagnetic. The magnetic particle transferrin may be bound to a dextran to enhance its uptake. Additional complexes found to be useful include platinum-rhodamine complexes, terbium complexes and heavy metal complexes, e.g., lanthanide complexes.

The principle upon which the present invention is based is grounded in the discovery that the HIV virus or a host cell infected therewith will transport, metabolize and/or sequester many elements or compounds in quite a different manner from that of the cells of the more advanced host organisms it usually infects. Note that HTLV-I infections result in deregulation of surface expression of the tranferrin receptor. (Vidal, J. Immun., 141, 984 (1988).) See also Gastl et al., Blut, 56:193 (1988). In one aspect of this invention, this specificity is thus used to selectively concentrate the above-mentioned particles within the virus or infected cells, with little or no uptake of said particles by normal host cells.

Thus, as mentioned, the particles introduced into the virus or viral-infected cells will generally be infectious organism-specific, i.e., an element or compound peculiar to the metabolism of the AIDS-causing organism being treated. Compounds which are particularly useful in this regard are any of the above-mentioned metal-chelating transport substances specific to the viruses and/or viral-infected cells. Also noteworthy in this process are such metal-containing organic structures as the porphyrins, including hematoporphyrins, cytochromes and chlorophylls. In addition to the naturally occurring porphyrins, mixed metal hybrid porphyrins may be prepared, substituting manganese, zinc, cobalt, chromium, nickel, platinum and rare earth series of metals such as dysprosium, erbium, europium, gallium, holmium, samarium, terbium, thulium ytterbium and yttrium. See the foregoing.

The minute particles described can be administered to the patient enterally, e.g., orally, parenterally, e.g., intravenously, intramuscularly, intraperitoneally, subcutaneously, topically, in suppository form, etc., depending upon the nature and location of the infection. Dosage and frequency of administration may also vary depending upon the nature of the HIV virus or viral-infected cells, as can be routinely determined.

The next stage of the present invention, after particle localization, is differential killing of the virus and/or such killing, incapacitating, cauterizing or altering of the viral-infected cells by causing inductive heating using a high frequency alternating electromagnetic field bringing about a precisely controllable rise in temperature or elevation in level of energy. Equivalently, pulsed electromagnetic fields and radiation (e.g., from a laser) and variants and combinations can also be employed. The principle of inductive heating through the use of hysteresis is a well known principle. Similarly, the monitoring of the temperatures of the living cells is a presently available technique well known to medical science. See the Gordon patents.

Inductive heating of the minute particles is achieved through use of an electric oscillator operating in the high frequency range which heats the particles by subjecting them to an intense high-frequency field within a large but otherwise conventional helical coil, field energy being converted to heat through hysteresis losses and the resistive dissipation of eddy currents. The helical induction coil is of sufficient internal diameter to permit the patient to pass within and of such length to encompass the length of the patient. Preferably, the internal diameter is greater than 3–6 feet, since diameters of inductive coils greater than 6 feet have a preferential effect on the overall process by providing a more uniform flux gradient to the patient. See the Gordon patents. However, smaller diameters, e.g., about 1 meter or so are also applicable. Moreover, the length could be approximately 20 centimeters with provision for scanning the body. Coils of other shapes strategically placed could also be utilized in achieving the coupling of the electromagnetic energy to the particles.

The frequency of the electromagnetic alternating high-frequency field will range from 1 kilohertz to 100 megahertz, preferably about 400 kHz, and the power input of the oscillator-generator will range from 1 kilowatt to 30 kilowatts per kg of patient body weight. 1 kilowatt of power per 1.0 kilogram of body weight is particularly useful. In this power and frequency range, the coils are selected to produce from 1 to $5 \times 10^4$ oersteds, preferably from 10 to 10,000 oersteds. Times are generally in the range of several seconds to several hours. The higher the intensity, the shorter the time period necessary to kill the HIV virus. Preferably, a high intensity, short time period will be used to cause a significant rise in particle temperature and to effectively kill the HIV virus.

The time necessary to inductively heat the minute particles near, within or attached to the HIV virus depends substantially upon the frequency and the power production of the alternating electromagnetic field and ultimately the strength of the field produced. Similarly, for the viral-infected cells to produce alteration in cell function or cell death, the time of treatment may vary. It should be noted, however, that it is only necessary to raise the temperature of the virus or viral-infected cell to the minimum required to cause vital death. Thus, the concentration of particles in the vehicles and choice of variables with respect to the type and details of electromagnetic treatment are not critical. It is only necessary that the appropriate temperature be attained.

In a further embodiment of the invention, treatment may be accomplished by inductive heating of magnetic particles endogenous to the HIV virus or viral-infected cells. As noted above, many types of viruses or viral-infected cells possess magnetic field-sensitive, e.g., metal-containing compounds. Some of these are altered when the virus is in the cell and hence are more susceptible to treatment per this invention with an alternating electromagnetic field. Among these particles are storage proteins and metabolically essential porphyrins such as hematoporphyrins, chlorophylis, cytochromes or nuclear protein materials. This aspect can also be based on the binding of Fe and metal ions to nuclear protein which is well known. Iron-sulphur storage proteins, cytochromes or ferritin can also form the basis for this aspect since they often differ in virus or viral-infected cells as compared to normal host cells.

Recently it has been demonstrated that ferritin will bind to the glycoprotein envelope of the AIDS virus (HTLV virus) (Hausmann, Journ. of Virological Methods, 1987, May 16 (1–2), pgs. 125–37). This is a basis for a particularly preferred aspect of this invention. Thus, ferritin particles or ferritin attached to a magnetic particle may be used in this invention, both for diagnostic purposes as described herein as well as for treatment with an alternating electromagnetic field.

The preferential uptake of particles by HIV virus-containing tissue is understandable, for example, in view of the alterations occurring in endothelial cells and the defective cells just as with endothelial groups in AIDS lesions (Schenk et al, Archives of Oto-Rhino-Laryngology, 1985, 242(3), pg. 305–13). The increased incidence of intramitochondrial iron in HIV virus-containing cells has also been demonstrated. (Sidhu G. S., et al, Human Pathology, 1985, Apr. 16 (4), pg. 377–86). This alteration in mitochondrial iron provides one means of utilizing endogenous ferromagnetic and/or paramagnetic centers to kill viruses or cells or to affect intracellular behavior and function in virus-containing cells. Thus, in general, uptake of virus of a cell will further alter and enhance its ability to selectively absorb particles.

The differences in structure between HIV virus or infected cell magnetic sensitive material or metal-containing compounds and those of normal host cells imply differences in magnetic characteristics, such as magnetic susceptibility, between the pathogen's compounds or those of infected cells and those of the normal host cells. Magnetic susceptibility is known to be temperature dependent and may be routinely measured by magnetometer devices. By measuring the magnetic susceptibilities or other magnetic properties of particles at certain temperatures, it is possible to calibrate the magnetometer equipment so that measurement of magnetic susceptibility, and thus the differences mentioned above, indicate the exact temperature of the particle in question. This capability may be used to selectively monitor and/or map the internal temperature of the invading HIV virus (as described by R. T. Gordon in U.S. Pat. Nos. 4,106,488 and 4,735,796 for the treatment of cancer cells) by focusing on the magnetic susceptibility of a magnetically sensitive entity, e.g., a particle unique to the pathogen. Of course, as described, a precise rise in temperature sufficient to kill the pathogenic HIV virus and/or infected cells without harming the host cells can also be effected.

The benefits of this approach to the patient are many. For example, there is little discomfort to the patient, no anesthetic is required, and the procedure is comparatively risk-free for the patient.

A further embodiment of the invention is the surface sterilization of objects using ferromagnetic, paramagnetic or diamagnetic particles. In this application of the invention, unsterile objects contaminated with HIV virus may be immersed in a solution containing said particles, which may be in the form of any of the compounds or elements mentioned in the previous embodiments. The concentration of the particles in solution would not be critical. The contaminating viruses would, over a period of time, take up the particles or attach the particles. A high-frequency alternating magnetic field could then be applied to the objects, raising the internal temperature of the contaminating HIV organism by inductive heating and eventually killing them. Because of the nature of this application of the invention, precise control of the temperature rise below a certain level would not be necessary, since no host cells are involved. This method provides a unique way of ridding objects, such as surgical instruments, of potentially dangerous viruses such as AIDS-causing viruses.

In addition, the particles of the invention may be used to diagnose, evaluate, monitor and/or locate (map) the viral infection in the host organism, e.g., by forming a temperature contour map since the particles bind to the virus or the viral-infected cell and the particles are also magnetically responsive, by using magnetic mapping techniques, e.g., using a magnetometer, e.g., a SQUID magnetometer, the presence and location of the virus can be determined. Similarly, magnetic resonance imaging (MRI) techniques as well as electron paramagnetic resonance (EPR) and electron spin resonance (ESR) methods can be used. See, e.g., Shaba et al., Computerized Radiol. Vol. II, No. 2, 69–73 (1987); Radiography, Jan/Feb 1986, Vol. 52, No. 60, 10.

It has been discovered also that increased oxygen delivery to enhance the temperature rise and the energy delivery to the HIV virus as well as to the virus-infected cells can also be utilized. See the Gordon U.S. Pat. No. 4,569,836 which uses such a technique for cancer cells and does not imply any correlation to viruses. Nevertheless, it has been discovered that the methods of this patent are fully applicable herein. A hyperbaric chamber has been useful in this regard when used prior to, during or after the treatment or diagnosis of this invention. It has been discovered also that chemical modification of the metabolic rate, e.g., through the use of glucose, substrate or oxidative or reductive agents is useful to help alter the virus and virus-infected cells per this invention. These techniques can be used to enhance virus or cell destruction. Such agents also include mitochondrial active agents which selectively affect oxidative phosphorylation and energy activity in the viral-infected cells. A combination of such agents, such as oxygen and an agent which affects oxidative phosphorylation or other metabolic step, or two other chemical agents per this invention, can be used to affect the HIV virus and/or the viral-infected cells, in accordance with this invention.

In a further advantageous aspect, the presence of the HIV virus in the cell alters its structure and the way in which the viral-infected cell behaves and functions. Included is an alteration in the charge on the cell membrane which affects the way in which the cell takes up particles which enhances the effect of this invention. The virus' presence also enhances some receptor systems of the viral-infected cell. Similarly, there is an effect on mitochondrial structure and function, as well as on nuclear protein and other subcellular components. These effects are utilized to advantage by this invention by using the combination of particles and an external field to produce the desired effects and/or chemical modifications discussed herein, e.g., of the internal energy level and/or the oxidative state of virus-infected cells, thus to alter the virus-infected cells' function or to destroy the virus and/or the infected cells.

This invention also relates to a variety of other advantageous methods for treating and/or diagnosing viruses, viral diseases and/or virus-containing cells. For example, in accordance with this invention, viruses or viral-infected cells, particularly HIV-type viruses, can be treated by altering the oxygen delivery to the virus or viral-containing cells. In a preferred mode, the oxygen delivery is enhanced by subjecting the cells or the host containing the cells to hyperbaric air or oxygen. This procedure, as mentioned above, is especially useful in conjunction with the heat-raising feature of this invention since the oxygen treatment enhances metabolism thereby further increasing temperature. With regard to oxygenation of the HIV virus, see Foster et al, New York State Journal of Medicine, May 1987, 280. As with other features of this invention, this particular aspect is applicable to viruses of all sorts, i.e., both RNA and DNA viruses, and especially HIV-type viruses and its variants or other AIDS-causing viruses.

More generally in this regard, this invention includes methods of treating HIV viruses or cells infected thereby by altering the respective metabolic rates by any physical or chemical means. The theory of this treatment is essentially the same as that for the oxygenation mentioned above, i.e., increased metabolism enhances the heat-killing Step of this invention, e.g., by increasing temperature and/or producing free radicals (analogous to singlet oxygen production above), which contribute to the effectiveness of weakening or destroying the virus or viral infected cell. For example, treatment may be effected by utilizing chemical or physical means to effect oxidative phosphorylation in the mitochondria of viral-infected cells or by controlling glucose delivered to such cells or to the virus per se. The former effect may be achieved for example by monensin which is an ionophase. This agent acts to alter the ion concentration in the mitochondria by affecting mitochondrial membrane permeability. The latter effect can be achieved for example by using glucose carrying agents, such as 2-deoxyglucose, The cell's metabolic activity can also be affected by an agent such as $H_2O_2$ which when delivered to the cell reacts with other chemical agents already present to produce singlet oxygen.

Again, these techniques for altering the metabolic rates of viruses or viral-containing cells are especially useful in conjunction with the underlying method of this invention involving the heat-killing of viruses or cells infected thereby. For example, in all of these methods, one useful chemical means of altering metabolic rate is by administration of conventional drugs which in any of a variety of ways affect metabolic rates. For example, AZT could be coadministered in conjunction with this invention.

In another aspect of this feature, a combination of chemical agents can be administered. Each of these can itself be active or the agents when separate could be inactive but when made simultaneously bioavailable, they can act together to have an effect on metabolic rate as described above.

In yet another aspect of this invention, the treatments of this invention will in fact effect a killing or other inactivation of the viruses or virus-containing cells but will not completely inactivate all of the cells. However, the mere decrease in the number of cells will enhance the ability of the body or the cells per se to immunologically inactivate the remaining virus. This is analogous to the situation with cancer where decreasing the tumor load helps the body develop a capability to destroy the remaining cells.

Through the use of heat per this invention to destroy the infected cells and/or virus, immunological stimulation is definitely enhanced. One mechanism for this enhancement is the release of immunologically active proteins from the destroyed infected cells and/or virus. This helps in immunological recognition of the infected cells and virus by uncovering immunologically important antigens.

This invention also produces other important and beneficial biophysical alterations including, for example, intracellular production of interferon and interleukins based on the response of cells to the treatment of this invention. Membrane, nuclear and cytoplasmic alterations which result therefrom are consistent with the production of these substances. In addition, production of these substances is a natural reaction to a foreign body type reaction. Thus, the biophysical alterations produced by this process create a very strong foreign body type reaction, especially where there is a foreign particle in the cell or virus which is then activated by an external electromagnetic field to increase the reaction even further.

In yet another feature of this invention, the various treatments and/or diagnoses of this invention can be carried out, not only inside a body, e.g., that of a mammal, including humans, but also outside such a body. This can be effected by administering the particles to the body and then removing a suitable body fluid, e.g., blood, or tissue from the body and performing a treatment or diagnosis per this invention outside the body, thereafter replacing the bodily fluid or tissue. Alternatively, the fluid or tissue can be removed from the body and then the particles can be administered, followed by a diagnostic or treatment step of this invention. This aspect of the invention can be carried out fully conventionally by utilizing readily available equipment, tubing, pumps, etc. In another alternative, the magnetic properties of the particles can be used in conjunction with an external magnetic field to simply remove the virus and/or viral-containing cells from the body sample.

It is also possible to affect viruses or viral-containing cells, e.g., alter their functions or inactivate them, by applying a physical or chemical treatment which affects the dipole moment of chemical entities in said viruses or cells including subcellular structures. Chemical entities having such dipole moments include substances such as ferritin, Fe-containing enzymes of the oxidative phosphorylation mechanism and other metal-containing enzymes in the cell. In addition, nucleic acids are often associated with metals and possess a dipole moment. This invention takes advantage of these entities by utilizing them to enhance or create the effects described above. For example, through the application of a constant magnetic field (e.g., of 100 gauss to 80 kgauss), the various dipoles in the infected virus or cell will be aligned. In addition, the dipole strengths are enhanced. Therefore, with the resultant alignment and increased dipole moment, the interaction of the electromagnetic field per this invention with these dipole moments is greatly enhanced. These dipole moments can also be affected by chemical means which are contemplated as full equivalents, e.g., the position of protein adjuncts or other substances will affect the overall dipole of the structure. Some of these structures are small combi-combinations of molecules (e.g., oxidative phosphorylation enzymes) and some are large combinations (e.g., ferritin). The dipole moment can thus be affected chemcally or physically and this will assist in the interaction with the alternating electromagnetic field and with the subsequent heating and inactivation of the infected cell and/or virus.

Suitable static field intensities are 300-100 oersteds. The field can be applied either before or during the treatment with the alternating electromagnetic field and can be used whenever one wishes to augment the effect via the dipoles already present. Both electric and magnetic fields of equivalent strengths are applicable. The advantages of this constant field adjunct aspect apply to all uses of this invention, e.g., therapeutic, diagnostic, etc.

In another aspect of this invention, it has been discovered that alterations in dielectric properties, e.g., conductivity and/or frequency-dependent dispersion curves as a function of temperature can also be used to measure cell temperatures and thereby map viruses analogously to the mapping by measurement of temperature per the above or of magnetic properties such as magnetic susceptibility per the Gordon patents. That is, measurements, typically along three orthogonal axes, using fully conventional equipment for measuring the dielectric properties, conductivity and/or frequency-dependent dispersion curves, will provide the desired map using fully conventional procedures, e.g., computer analyses.

These effects reflect the interaction of electric dipoles in tissue with the external electric field. They are temperature-related since the orientation of the dipoles affects the temperature and/or is affected by the temperature, e.g., the higher the temperature, the less the orientation of the dipoles. Administration of particles will affect these properties. Analysis of these parameters, e.g., the frequency dependent dispersion curves, will reflect the changes in temperature in the infected cells and/or viruses and/or their metabolic rates. Therefore, these measurements can also be used to monitor the temperature and/or metabolism in the infected tissues and cells. Alterations in dielectric properties such as conductivity and frequency dispersion curves will be correlated with temperature and the metabolism of the infected cells and/or virus. As an example, the frequency dispersion curves map the response of the tissue with regard to conductivity over a given frequency range. This produces a curve of conductivity vs. frequency. This curve will change as the temperature changes. By routine methods of standardization, these changes can be readily correlated with temperature or metabolic rate changes by comparison with a standard calibration curve constructed from a series of such measurements, for example. This aspect of the invention will provide valuable information, e.g., in diagnosing viral diseases or in timing the administration according to the heating method of this invention. Such information will also provide valuable data regarding the distribution of viruses in a cell population.

In yet another aspect of this invention, the particles which are administered, instead of or in addition to being inductively heatable, will also be susceptible to acoustic waves, especially ultrasound. They will accordingly enhance the effect of ultrasound on the virus or viral-containing cells. This will beneficially affect intracellular and/or extracellular events. For example, the interaction of acoustic waves with tissue is related to the density and properties of the tissue involved, e.g., molecular spacing, inhomoge-neities, etc. Through the addition of particles, these properties can be altered. As an example, particles can increase the density of infected cells and/or viruses and help to increase the absorption of acoustic energy. In general, particles with a higher mass will increase the density to a greater degree, such as ferritin or heavy mass particles. Ultrasound will induce vibration effects on the particles and will thus serve to facilitate and to stimulate intracellular events.

The vibrational effect on the particles induced by ultrasound, and which may even be induced by the oscillating electromagnetic field, will serve to enhance the alteration of intracellular events as described above, including the stimulation of immunological factors. An alternating electromagnetic field between 1 Hz and 500 MHz can also be used to affect said particles and make them more or less responsive to an exciting alternating electromagnetic field produced by magnetostrictive induced vibrations applied to said viral containing cells and viruses. Thus, the particles can be selected to include compositions that specifically affect intracellular and extracellular events in said viral containing tissue and viruses or said particles can be treated to make them more or less responsive to an exciting alternating electromagnetic field produced by magnetostrictive induced vibrations. Furthermore, an alternating electromagnetic field can be applied to said particles to produce acoustic changes in them and affect the cellular and subcellular structures of said viral containing tissues and/or viruses. These vibrational effects will also facilitate the absorption of the particles by the cells by easing its entry through the cell membrane. The capability of ultrasound to affect particles is well-documented by recent extensive work in which ultrasound is used to breakup gallstones and kidney stones. Furthermore, the application of ultrasound in this invention will also have utility in the various diagnostic techniques mentioned above to monitor the processes involved.

Without further elaboration, it is believed that one skilled in the art can, using the preceding description, utilize the present invention to its fullest extent.

The entire text of all applications, patents and publications, cited above are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An in vitro method of diagnosing HIV viral disease or an HIV viral infection in a cell of or from a living host comprising:

introducing in vitro into a locus of said virus or cells, particles localizable near, in or on the virus or viral-infected cells, such particles being capable of responding to a magnetic field and being of a size less than 1 micron, whereby the particles are selectively located near, into or on the virus and/or viral-infected cells, wherein said particles are magnetic metal transferrin particles, and measuring a magnetic property of the particles.

2. A method of claim 1 wherein said measuring provides a map which identifies the location and/or the concentration of the particles.

3. A method according to claim 2 wherein a SQUID magnetometer is used for the magnetic mapping.

4. A method according to claim 2 wherein nuclear magnetic resonance is used to map the particles.

5. A method according to claim 2 wherein EPR or ESR is used to map the particles.

6. A method according to claim 1 wherein said virus is an AIDS-causing virus.

7. A method according to claim 1 wherein said particles comprise a metal which is cobalt, zinc, chromium, nickel, platinum, manganese, a rare earth metal, dysprosium, erbium, gallium, holmium, samarium, terbium, thulium, ytterbium, yttrium or iron.

8. A method of claim 1 wherein said magnetic particle is ferromagnetic, paramagnetic or diamagnetic.

9. A method of claim 1 wherein the magnetic particle transferrin is bound to dextran.

10. A method of claim 1 wherein the particle is $Fe_3O_4$-dextran-transferrin.

* * * * *